US009717839B2

(12) United States Patent
Hashimoto

(10) Patent No.: US 9,717,839 B2
(45) Date of Patent: Aug. 1, 2017

(54) EXTRACORPOREAL CIRCULATION DEVICE

(71) Applicant: TERUMO KABUSHIKI KAISHA, Tokyo (JP)

(72) Inventor: Tomoaki Hashimoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/075,360

(22) Filed: Mar. 21, 2016

(65) Prior Publication Data
US 2016/0199563 A1 Jul. 14, 2016

Related U.S. Application Data

(63) Continuation of application No. PCT/JP2014/074119, filed on Sep. 11, 2014.

(30) Foreign Application Priority Data

Sep. 24, 2013 (JP) ................................. 2013-197307

(51) Int. Cl.
*H02P 3/06* (2006.01)
*A61M 1/36* (2006.01)
*A61M 1/10* (2006.01)
*A61M 1/32* (2006.01)

(52) U.S. Cl.
CPC .......... *A61M 1/3607* (2014.02); *A61M 1/101* (2013.01); *A61M 1/1086* (2013.01); *A61M 1/32* (2013.01); *A61M 1/3666* (2013.01); *H02P 3/06* (2013.01)

(58) Field of Classification Search
CPC ....................................................... H02P 3/06
USPC .......................................... 318/490, 34, 558
See application file for complete search history.

(56) References Cited

U.S. PATENT DOCUMENTS

| 5,437,634 | A | 8/1995 | Amano |
| 5,894,273 | A | 4/1999 | Meador et al. |
| 6,183,412 | B1 * | 2/2001 | Benkowski ........... A61M 1/101 600/16 |
| 6,220,747 | B1 * | 4/2001 | Gosselin ........... B01F 15/00253 137/3 |
| 8,905,910 | B2 * | 12/2014 | Reichenbach ...... A61M 1/1086 600/16 |

FOREIGN PATENT DOCUMENTS

| JP | 05-048439 | 2/1993 |
| JP | 2010-194101 | 9/2010 |
| JP | 2011-065889 | 3/2011 |

* cited by examiner

*Primary Examiner* — David S Luo
(74) *Attorney, Agent, or Firm* — MacMillan, Sobanski & Todd, LLC

(57) ABSTRACT

An extracorporeal blood circulator includes a control unit and a speed manipulation section. A rotation display section displays a lower limit rotation setting value of a pump motor in accordance with a command of the control unit. The lower limit rotation speed setting value is a minimum rotation speed for preventing backflow of blood inside a circulation circuit A manually adjusted speed setting request from the manipulation section controls the pump speed, except that the controller enforces the lower limit speed setting unless receiving confirmation from a manipulator.

5 Claims, 8 Drawing Sheets

EXTRACORPOREAL CIRCULATION DEVICE

This application is a continuation of PCT Application No. PCT/JP2014/074119, filed Sep. 11, 2014, based on and claiming priority to Japanese application no. 2013-197307, filed Sep. 24, 2013, both of which are incorporated herein by reference in their entirety.

TECHNICAL FIELD

The present invention relates to an extracorporeal circulator which transports blood to the outside of a patient and circulates the blood.

BACKGROUND ART

For example, in a case where cardiac surgery of a patient is performed, extracorporeal blood circulation is performed in which a pump is driven by using a motor of an extracorporeal circulator so that blood is removed from the vein (e.g., the vena cava) of the patient, exchange of oxygen gas in the blood is performed through an artificial lung, and then the blood is returned to the artery (e.g., the aorta) of the patient again.

In the extracorporeal circulator, it is important that a lower limit rotation speed of the pump motor is maintained during the time that the patient receives extracorporeal blood flow from the circulator. The lower limit rotation speed of the pump motor denotes a minimum rotation speed for preventing backflow of blood inside a circulation circuit 1R (FIG. 1) when the pump motor is operated so as to cause the blood to return from the artificial lung (artificial heart and lung) to the inside of the body of a patient. If the rotation speed of the motor drops to the lower limit rotation speed or lower, backflow of blood may occur in the circulation circuit and may affect the body of the patient. Thus, it is important that the pump speed that is manually commanded via a control knob on a control unit by a manipulator remains at or above the lower limit rotation speed of the motor. On the other hand, the manipulator needs to have the ability to command a pump speed below the lower limit rotation speed during other stages of the cardiac surgery (such as coast down in order to disconnect the patient from the extracorporeal circulator.

Japanese publication JP-A-5-48439 discloses a counter device which is attached to various types of industrial instruments and performs various types of control by counting the number of times of operations of the instrument. The counter device has a case, a counting setting unit which is provided in the case, a display section which displays a current counting value, an upper limit setting value display section, and a lower limit setting value display section. The case displays a setting value, an upper limit setting value, and a lower limit setting value. The counter device has the upper limit setting value display section and the lower limit setting value display section which respectively set the upper limit setting value and the lower limit setting value. Even in a case where the setting value is erroneously changed during an operation of the instrument, the operation of a system is smoothly maintained by performing counting-up while using the upper limit setting value or the lower limit setting value which is set to a predetermined setting value. During the operation, the setting value can be changed within a range between the upper limit setting value and the lower limit setting value.

SUMMARY OF INVENTION

Technical Problem

When performing extracorporeal circulation manipulation, there has been a possibility that a commanded rotation speed of a motor inadvertently drops to a speed at a lower limit rotation speed or lower in an extracorporeal circulator.

Depending on certain factors such as the size or health of the patient, appropriate values for the rotation speed of the pump motor can be identified by a manipulator (e.g., surgical personnel) prior to initiating extracorporeal circulation. Upper and lower limits for the rotation speed are also identified, which may take into account size or health of the patient or may be set by hospital policy or by adopting standard recommended limits, for example. Potential cases where the rotation speed drops to the lower limit rotation speed or lower includes a case where a manipulator forgets the correct value of the lower limit rotation speed to be maintained and manually sets an erroneous numerical value of the lower limit rotation speed, a case where the body of a manipulator erroneously comes into contact with (i.e., bumps into) a rotary knob for setting the rotation speed and the rotary knob inadvertently rotates so that the rotation speed of the motor is set to the lower limit rotation speed or lower, a case where an object falls and hits the rotary knob and the rotary knob rotates so that the rotation speed of the motor is accidentally set to the lower limit rotation speed or lower, and the like.

However, according to the technique disclosed in Japanese publication JP-A-5-48439, in a counter device, even in a case where a commanded value is erroneously changed during an operation of an instrument, the operation of a system is maintained by only performing counting-up while using an upper limit setting value or a lower limit setting value which is set to a predetermined setting value, and no method has been devised for preventing the rotation speed of the motor from being set to the lower limit rotation speed which is a dangerous level, on the basis of every contingency.

An object of the present invention is to provide an extracorporeal circulator in which extracorporeal circulation manipulation can be safely performed during a surgical operation while erroneous manipulation causing a rotation speed of a rotation drive unit to drop to a lower limit rotation speed or lower is prevented in the extracorporeal circulator.

Solution to Problem

According to the present invention, there is provided an extracorporeal circulator in which a pump arranged in a circulation circuit is driven by a rotation drive unit and blood of a patient is circulated outside a body. The extracorporeal circulator includes a control unit, a manipulation section coupled with the control unit to set a rotation speed setting value of the rotation drive unit in a changeable manner, and a rotation speed display section that is able to display the lower limit rotation setting value of the rotation drive unit in accordance with a command of the control unit. The lower limit rotation speed setting value is a minimum rotation speed for preventing backflow of blood inside the circulation circuit when a manipulator performs manipulation so as to operate the rotation drive unit and to cause the blood to return to an inside of the body of the patient.

According to the above-described configuration, the lower limit rotation speed setting value of the rotation drive unit can be changed by using the control unit and the manipulation section, and the rotation display section can display the lower limit rotation speed setting value of the rotation drive unit. Accordingly, since the lower limit rotation speed of the rotation drive unit can be visually and clearly checked in the extracorporeal circulator, it is possible to prevent erroneous manipulation that would result in adjustment of the rotation speed to drop to the lower limit rotation speed or lower, and it is possible to prevent backflow of blood from occurring in the circulation circuit and affecting the body of the patient. Thus, it is possible to safely perform extracorporeal circulation manipulation during a surgical operation.

It is preferable that after a rotation speed of the rotation drive unit is raised and exceeds the lower limit rotation speed setting value, the control unit afterwards causes the display section to display a confirmation message before the rotation speed of the rotation drive unit is permitted to be reduced to the lower limit rotation speed setting value or lower.

According to the above-described configuration, since the control unit causes the display section to display a confirmation message before the rotation speed of the rotation drive unit is reduced to the lower limit rotation speed setting value or lower, the confirmation message allows a manipulator to visually check whether the rotation speed of the rotation drive unit is set to the lower limit rotation speed setting value or lower, and thus, it is possible to prevent the rotation speed of the rotation drive unit from being erroneously manipulated and being set to the lower limit rotation speed setting value or lower.

It is preferable that when the confirmation message displayed by the display section is received, the control unit allows the rotation speed of the rotation drive unit to be reduced to the lower limit rotation speed setting value or lower after being confirmed by the manipulator.

According to the above-described configuration, in a case where the confirmation message displayed by the display section is received, a manipulator can reduce the rotation speed of the rotation drive unit to the lower limit rotation speed setting value or lower, and thus, it is possible to prevent the rotation speed of the rotation drive unit from being erroneously manipulated and being set to the lower limit rotation speed setting value or lower.

It is preferable that the manipulation section is a rotary manipulation section having a rotary knob which is able to be rotatably manipulated as the manipulator pinches the rotary knob with fingers, and the rotation speed display section which is lit to display the rotation speed of the rotation drive unit is provided on the periphery of the rotary knob.

According to the above-described configuration, since the rotation speed display section is provided on the periphery of the rotary knob, when a manipulator manipulates the rotary knob, it is possible to visually check the rotation speed of the rotation drive unit in relation to the lower limit due to lighting of the rotation speed display section.

It is preferable in one embodiment to provide a knob mechanism to physically prevent manipulation causing a speed setting below a lower limit, wherein the rotary manipulation section has a fixed portion; a rotary portion which is provided so as to be rotatable with respect to the fixed portion in order to arbitrarily set the lower limit rotation speed setting value of the rotation drive unit; and the rotary knob which is provided so as to be rotatable with respect to the rotary portion and the fixed portion, and is rotatably manipulated by being pinched by the manipulator in order to set the rotation speed of the rotation drive unit and apply a command to the control unit. It is preferable that the rotary portion has an erroneous manipulation prevention portion which abuts on the rotary knob so as to prevent the rotary knob from erroneously rotating and being set to the lower limit rotation speed setting value or lower of the rotation drive unit.

According to the above-described configuration, since the rotary portion has the erroneous manipulation prevention portion which abuts on the rotary knob so as to prevent the rotary knob from erroneously rotating to the lower limit rotation speed setting value or lower of the rotation drive unit, it is possible to mechanically and reliably prevent the rotation speed of the rotation drive unit from being erroneously manipulated and being set to the lower limit rotation speed setting value or lower.

Advantageous Effect of Invention

According to the present invention, it is possible to provide an extracorporeal circulator in which extracorporeal circulation manipulation can be safely performed during a surgical operation while erroneous manipulation causing a rotation speed of a rotation drive unit to drop to a lower limit rotation speed or lower is prevented in the extracorporeal circulator.

DESCRIPTION OF EMBODIMENT

Hereinafter, a preferable embodiment of the present invention will be described in detail with reference to the drawings.

Since the below-described embodiment is a suitable specification example of the present invention, the embodiment is subjected to various types of limitations which are technically preferable. However, the scope of the present invention is not limited to the aspects thereof unless otherwise stated in the following description particularly limiting the present invention.

Figure 1:
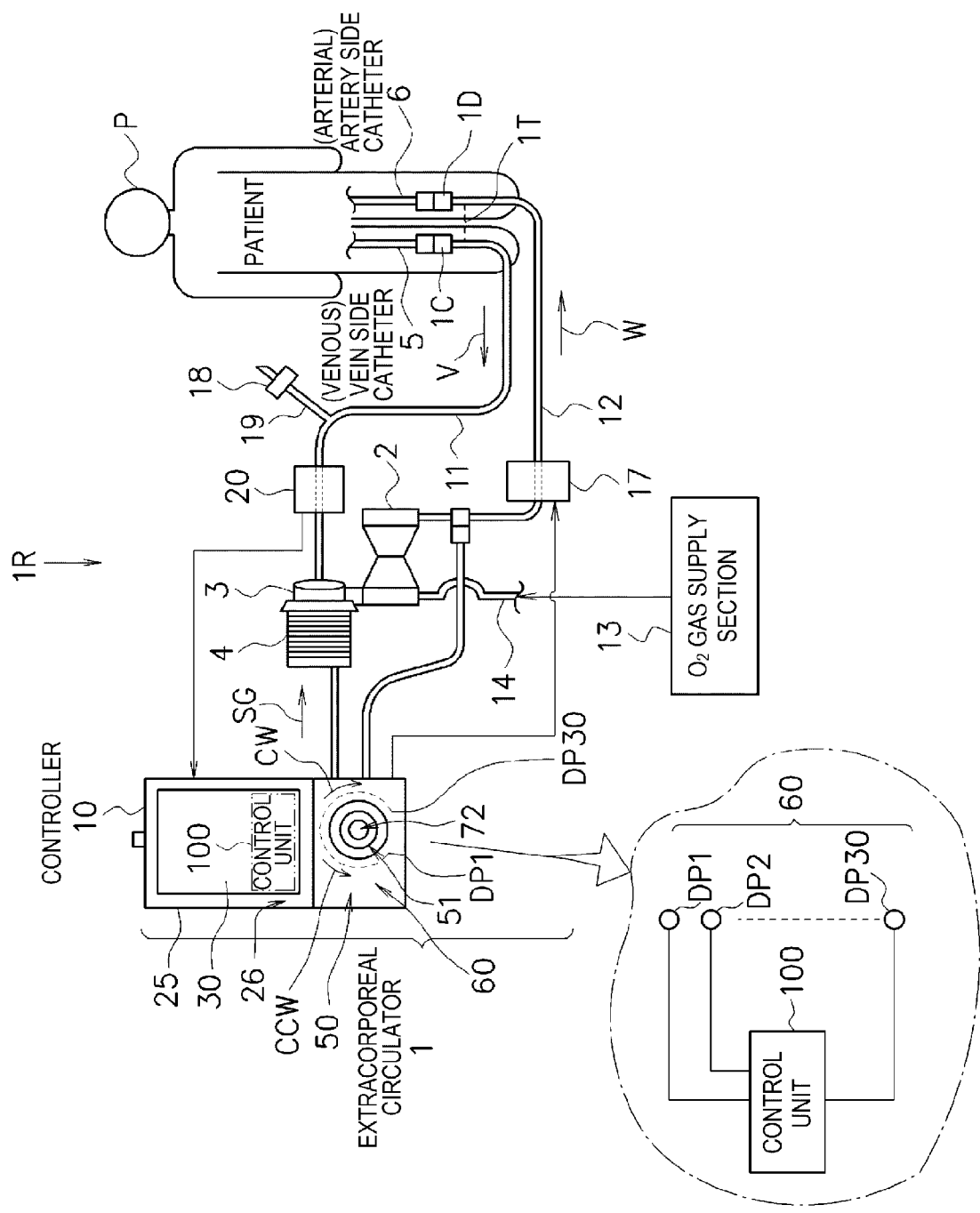
FIG. 1 is a system diagram illustrating a preferable embodiment of an extracorporeal circulator of the present invention.

"Extracorporeal circulation" performed by an extracorporeal circulator 1 illustrated in FIG. 1 includes an "extracorporeal circulation operation" and an "assisting circulation operation". The extracorporeal circulator 1 can perform both the "extracorporeal circulation operation" and the "assisted circulation operation".

The "extracorporeal circulation operation" denotes a circulation operation of blood and a gas exchange operation (oxygenation and/or carbon dioxide removal) with respect to the blood performed by the extracorporeal circulator 1 in a case where blood circulation is temporarily stopped in the heart due to cardiac surgery, for example. The "assisted circulation operation" denotes assisting of the blood circulation operation which is also performed by the extracorporeal circulator 1 in a case where the heart of a patient P that is an application target of the extracorporeal circulator 1 cannot sufficiently function or in a state where the lung cannot sufficiently perform gas exchange. Some apparatuses have a function of the gas exchange operation performed with respect to blood.

In a case where cardiac surgery of the patient is performed, for example, the extracorporeal circulator 1 illustrated in FIG. 1 can perform artificial lung extracorporeal blood circulation including draining blood from the vein (the vena cava) of the patient by operating a pump of the extracorporeal circulator 1, replacing gas in the blood through an artificial lung so as to perform oxygenation of the blood and then returning the blood to the artery (the aorta) of the patient again. The extracorporeal circulator 1 is an apparatus which operates in place of the heart and the lung.

The extracorporeal circulator 1 illustrated in FIG. 1 has a circulation circuit 1R which circulates blood. The circulation circuit 1R includes an artificial lung 2, a centrifugal pump 3, a drive motor 4 which is drive means, a vein side catheter (venous catheter) 5, an artery side catheter (arterial catheter) 6, and a controller 10 which is an electronic control unit.

As illustrated in FIG. 1, the vein side catheter (venous catheter) 5 is inserted through the femoral vein, and a distal end of the vein side catheter 5 indwells in the right atrium. The artery side catheter (arterial catheter) 6 is inserted through the femoral artery. The vein side catheter 5 is connected to the centrifugal pump 3 by using a venous tube 11. The venous tube (also referred to as the venous line) 11 is a conduit line for supplying blood. When the drive motor 4 operates the centrifugal pump 3 in accordance with a command SG of the controller 10, the centrifugal pump 3 can drain blood through the venous tube 11, can cause the blood to pass through the artificial lung 2, and then, cause the blood to return to the patient P via an arterial tube 12 (also referred to as the arterial line).

The artificial lung 2 is arranged between the centrifugal pump 3 and the arterial tube 12. The artificial lung 2 performs the gas exchange operation (oxygenation and/or carbon dioxide removal) with respect to the blood. The artificial lung 2 is a membrane-type artificial lung, for example. It is particularly preferable to use a hollow fiber membrane-type artificial lung. Oxygen gas is supplied to the artificial lung 2 from an oxygen gas supply section 13 through a tube 14. The arterial tube 12 is a conduit line connecting the artificial lung 2 and the artery side catheter 6. For example, a conduit line made from a synthetic resin such as a vinyl chloride resin, and silicone rubber which are highly transparent and flexible can be used as the venous tube 11 and the arterial tube 12. Inside the venous tube 11, blood flows in a V-direction. Inside the arterial tube 12, blood flows in a W-direction.

As illustrated in FIG. 1, an ultrasonic air bubble detection sensor 20 is arranged outside the venous tube 11 in the middle of the venous tube 11.

A fast clamp 17 is arranged outside the arterial tube 12 in an intermediate position of the arterial tube 12.

In a case where the ultrasonic air bubble detection sensor 20 detects that an air bubble is present in blood which has been sent to the inside of the venous tube 11, the ultrasonic air bubble detection sensor 20 transmits a detection signal indicating that an air bubble has been detected, to the controller 10. Accordingly, the fast clamp 17 urgently blocks the arterial tube 12 in order to stop blood from being supplied to the patient P side in accordance with a command of the controller 10.

Incidentally, the drive motor 4 rotationally drives the centrifugal pump 3. A lower limit rotation speed setting value is set to the drive motor 4 and the centrifugal pump 3. The lower limit rotation speed of the drive motor 4 (the centrifugal pump 3) denotes a minimum rotation speed for preventing backflow of blood inside the circulation circuit 1R of the extracorporeal circulator 1 when a control unit 100 operates the drive motor 4 and drives the centrifugal pump 3 so as to cause the blood to return from the artificial lung 2. In other words, the lower limit rotation speed of the drive motor 4 (the centrifugal pump 3) is a rotation speed of the centrifugal pump when a pressure applied from the centrifugal pump 3 to blood in the arterial tube 12 is equal to the blood pressure of the patient P in the arterial tube 12.

If the rotation speed of the centrifugal pump 3 (the drive motor 4) is reduced to the lower limit rotation speed setting value or lower, backflow of blood may occur in the circulation circuit 1R and may affect the body of the patient P. Thus, for the circulation circuit 1R of the extracorporeal circulator 1 setting and maintaining of the lower limit rotation speed setting value are important.

As illustrated in FIG. 1, the controller 10 has a case 25, a display section 30, and a manipulation section 50. The display section 30 and the manipulation section 50 are arranged on the frontal surface of the case 25. The display section 30 is arranged on the upper side of a front surface portion 26 of the case 25 and can display various types of numerical values, a notification item such as a "confirmation message", a warning item, and the like. As the display section 30, for example, a liquid crystal display apparatus is employed. However, the display section 30 is not particularly limited. The various types of numerical values include the lower limit rotation speed setting value of the centrifugal pump 3, a current rotation speed, and the like.

The manipulation section 50 provided in the controller 10 as illustrated in FIG. 1 is arranged on the lower side of the front surface portion 26 of the case 25. The manipulation section 50 includes a rotary manipulation section 51 and a rotation speed display section 60. Control unit 100 controls an actual rotation speed of pump 3 in response to manually adjusted speed settings made by a manipulator via rotary manipulation section 51. Actual rotation speed of pump 3 may be directly proportional to the value as requested by the manual adjustment of rotary knob 72, except that the control unit 100 may impose the lower limit rotation speed setting value as described below. The rotation speed display section 60 is depicted so as to have an annular shape in the drawings. However, the arrangement shape thereof is not limited to the annular shape. For example, it is possible to execute various types of forms such as a straight-lined lever which moves in a guide unit, and a touch panel which is designed to have a curved shape.

In the embodiment, the rotary manipulation section 51 has a rotary knob 72. As a manipulator pinches (i.e., grasps) the rotary knob 72 with fingers and rotates the rotary knob 72 in a clockwise direction CW, the rotation speed of the centrifugal pump 3 can be increased. In addition, as a manipulator pinches the rotary knob 72 with fingers and rotates the rotary knob 72 in a counterclockwise direction CCW, the rotation speed of the centrifugal pump 3 can be decreased.

The rotation speed display section 60 is arranged on the periphery of the rotary manipulation section 51, and the rotation speed display section 60 is configured to have a plurality of light emitting elements, for example, thirty LED (light emitting diode) elements DP1 to DP30 which are arranged in an annular shape. The LED elements DP1 to DP30 can be selectively lighted in accordance with an actual pump speed as commanded to the control unit 100 of the controller 10 illustrated in FIG. 1 and can be preferably lighted in "red" or "green".

Subsequently, description will be given with reference to FIG. 2.

Figure 2:
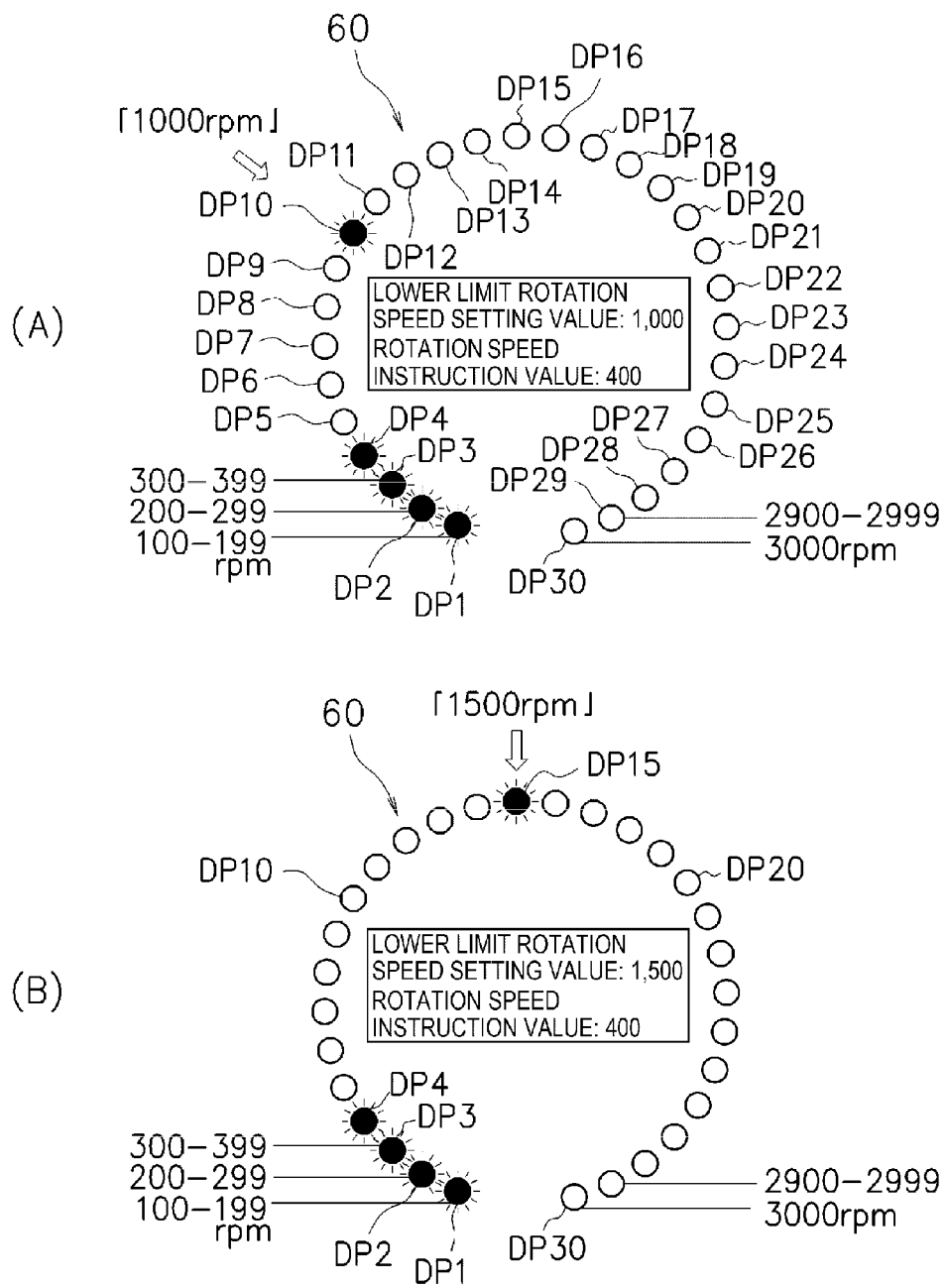
FIG. 2 is a diagram illustrating a lighting display example of a lighting display section of a controller.

FIG. 2 illustrates a lighting display example of the annular rotation speed display section 60 which is arranged in the controller 10. In the lighting display example of FIG. 2(A), the LED elements DP1 to DP4 and the LED element DP10 are selectively lighted in "red", and other LED elements are in non-lighting states. In the lighting display example of FIG. 2(B), the LED elements DP1 to DP4 and the LED element DP15 are lighted in "red", and other LED elements are in the non-lighting states. Thus, the "highest" one of the consecutively lit string of LED elements indicates the range within which the actual pump speed currently resides.

In the annular rotation speed display section 60 illustrated in FIGS. 2(A) and 2(B), the LED element DP1 indicates the rotation speed ranging from "100 rpm to 199 rpm", the LED element DP2 indicates the rotation speed ranging from "200 rpm to 299 rpm", the LED element DP3 indicates the rotation speed ranging from "300 rpm to 399 rpm", . . . , the LED element DP29 indicates the rotation speed ranging from "2,900 rpm to 2,999 rpm", and the LED element DP30 indicates the rotation speed of "3,000" rpm.

In the lighting display example of the rotation speed display section 60 illustrated in FIG. 2(A), the LED elements DP1 to DP4 and the LED element DP10 are lighted in "red". Therefore, the actual commanded value of rotation speed is 400 rpm, and the lower limit rotation speed setting value is 1,000 rpm. In the lighting display example of the rotation speed display section 60 illustrated in FIG. 2(B), the LED elements DP1 to DP4 and the LED element DP15 are lighted in "red". Therefore, the actual commanded value of rotation speed is 400 rpm, and the lower limit rotation speed setting value is 1,500 rpm. In other words, FIGS. 2(A) and 2(B) illustrate a display change example in a case where the lower limit rotation speed setting value has been changed from "1,000 rpm" to "1,500 rpm".

In FIGS. 2(A) and 2(B), each of the LED elements DP1 to DP4, the LED element DP10, and the LED element DP15 is lighted in "red", thereby attracting the attention of a manipulator.

Subsequently, description will be given with reference to another embodiment of the invention in FIG. 3.

Figure 3:
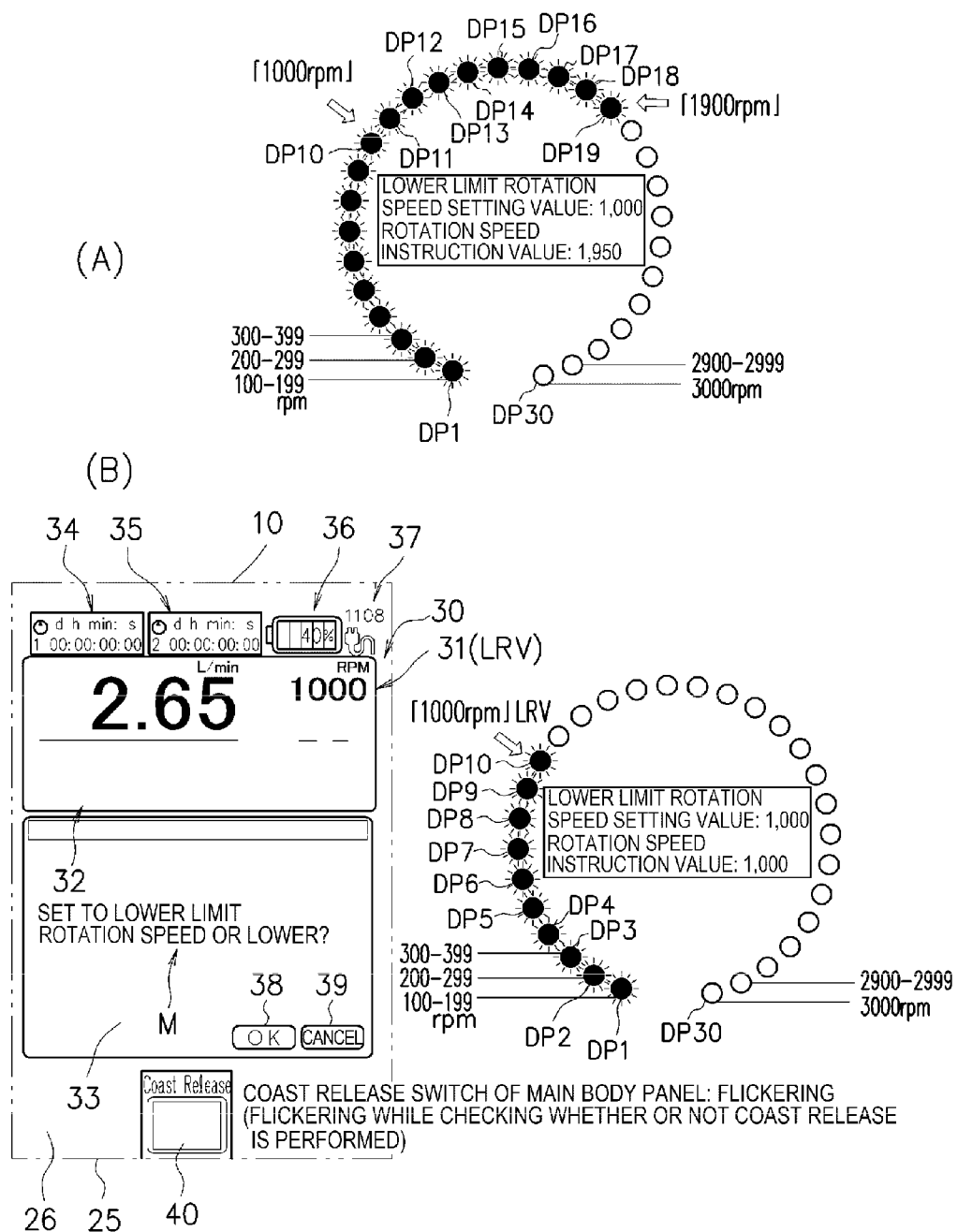
FIG. 3 is a diagram illustrating another lighting display example of the lighting display section of the controller different from the display example illustrated in FIG. 2.

The lighting display example of the rotation speed display section 60 of the controller 10 illustrated in FIG. 3 is different from the lighting display example of the rotation speed display section 60 illustrated in FIG. 2. In the lighting display example of the rotation speed display section 60 illustrated in FIG. 3(A), the LED elements DP1 to DP10 are lighted in "red", and the LED elements DP11 to DP19 are lighted in "green". In this lighting state, a coast (i.e., lower limit) rotation speed setting value is "1,000 rpm", and a rotation speed commanded value is set to "1,950 rpm".

In the lighting display example of the rotation speed display section 60 illustrated in FIG. 3(B), as a manipulator rotates the rotary manipulation section 51 illustrated in FIG. 1 in the counterclockwise direction CCW, the rotation speed instruction value indicates a state of being reduced to a "lower limit rotation speed setting value" LRV, that is, a state of being reduced from the rotation speed "1,950 rpm" illustrated in FIG. 3(A) to the rotation speed "1,000 rpm". Accordingly, FIG. 3(B) depicts that the LED elements DP1 to DP10 are lighted. As exemplified in FIG. 3(B), in such a state where the rotation speed is reduced to 1,000 rpm which is the "lower limit rotation speed setting value" LRV, a rotation speed display area 31 displays "1,000 rpm" as the lower limit rotation speed setting value LRV as illustrated in FIG. 3(B).

In FIGS. 3(A) and 3(B), each of the LED elements DP1 to DP10 is lighted in "red" so as to attract the attention of a manipulator. However, in FIG. 3(A), each of the LED elements DP11 to DP19 in which the rotation speed exceeds 1,000 rpm, that is, the lower limit rotation speed setting value LRV is lighted in "green" so as to be discriminated from "red", thereby notifying a manipulator that the rotation speed exceeds the lower limit rotation speed setting value LRV by lighting the LED elements DP11 to DP19 in "green".

FIG. 3(B) illustrates a display example of the display section 30 of the controller 10 illustrated in FIG. 1. The display section 30 has the rotation speed display area 31, a blood delivery quantity display area 32, a display area 33 for displaying a "confirmation message" M and the like, time display areas 34 and 35, a remaining battery power display area 36, and a time display area 37.

The rotation speed display area 31 displays the rotation speed of the drive motor 4 (the centrifugal pump 3). The blood delivery quantity display area 32 displays the blood delivery quantity (L/min). The display area 33 which displays a "confirmation message" can display the "confirmation message" M, for example, "Set to Lower Limit Rotation Speed or Lower?" and the like. The time display areas 34 and 35 display integral times and the like. The remaining battery power display area 36 displays the remaining power of a battery which is built in the controller 10. The time display area 37 performs digital display of the current time.

In the confirmation message display area 33, an "OK" button 38 and a "CANCEL" button 39 are arranged. The "OK" button 38 and the "CANCEL" button 39 are buttons which a manipulator touches with a finger so as to be able to indicate whether or not coast release is performed.

In addition, in the front surface portion 26 of the case 25 of the controller 10, a coast release button (the coast release switch) 40 is arranged. The coast release button 40 functions similar to the "OK" button 38 and is pressed in a case where coast release is performed. In addition, by causing the coast release button 40 to flicker while checking whether or not coast release is performed, it is possible to attract the attention of a manipulator.

The coast release denotes that the rotation speed of the drive motor 4 is set to the lower limit rotation speed setting value or lower.

It is necessary that the rotation speed which has been maintained above the lower limit during a procedure is reduced to the pre-set lower limit rotation speed setting value or lower by dropping the rotation speed to zero when the procedure of extracorporeal circulation ends and the circulation circuit 1R is separated from a patient. In this case, since the reduction of the rotation speed is not caused by erroneous manipulation, it is possible to cause the rotation speed to drop to the lower limit rotation speed or lower by pressing the "OK" button 38 or the coast release button 40. Then, the circulation circuit 1R can be separated only after the rotation speed becomes zero.

Here, description will be given with reference to FIG. 4 regarding an example of a flow of a procedure performed by a manipulator before extracorporeal circulation manipulation in the extracorporeal circulator 1 illustrated in FIG. 1 is performed, that is, a process of a procedure for preparation of a surgical operation before the start of extracorporeal circulation.

Figure 4:
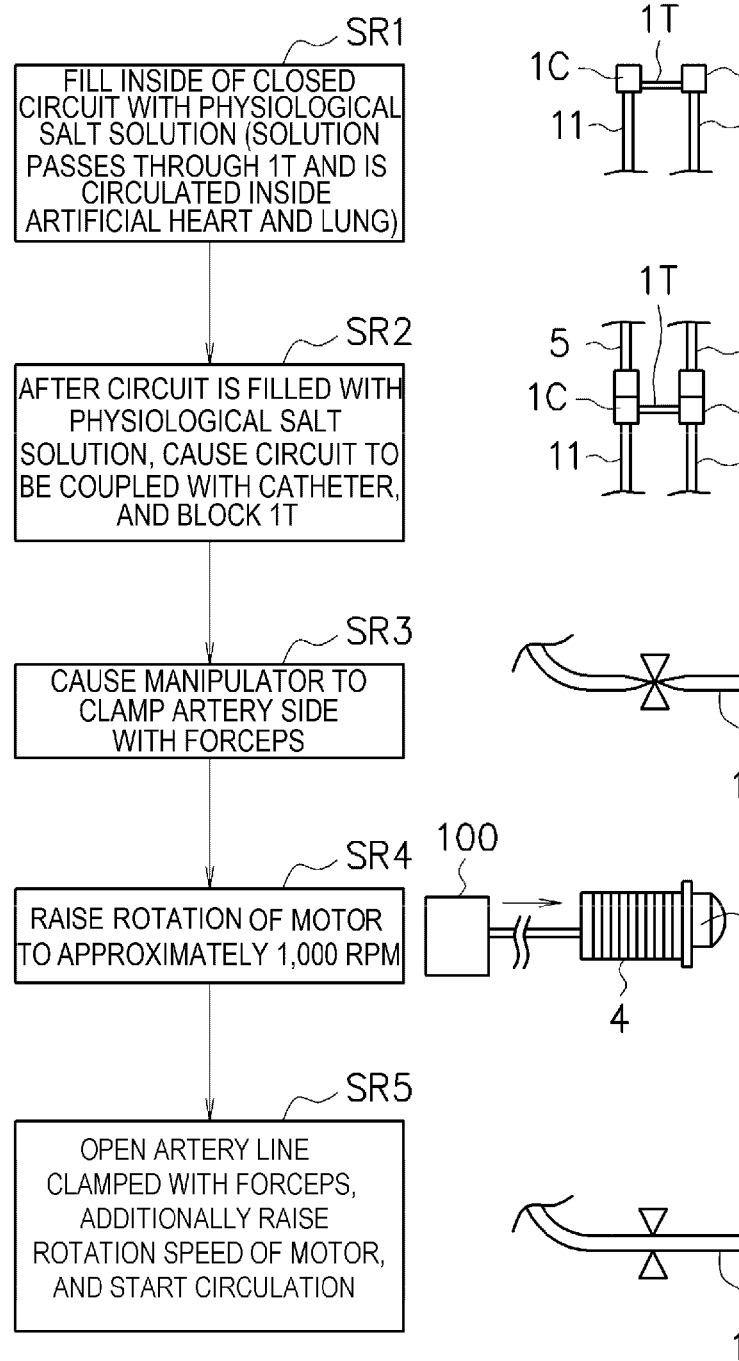
FIG. 4 is a flow chart illustrating a manipulation example in which the inside of a circulation circuit is filled with a physiological salt solution, a rotation speed of a drive motor is raised to approximately 1,000 rpm, and then, the rotation speed of the drive motor is additionally raised so as to start circulation.

FIG. 4 illustrates a manipulation example in which the inside of the circulation circuit 1R is filled with a physiological salt solution, the rotation speed of the drive motor 4 is raised to approximately 1,000 rpm, and then, the rotation speed of the drive motor 4 is additionally raised so as to start circulation.

As illustrated in FIG. 1, the vein side catheter 5 is inserted through the femoral vein of the patient P in advance, and the distal end of the vein side catheter 5 indwells in the right atrium. The artery side catheter 6 is inserted through the femoral artery. In Step SR1 in FIG. 4, the circulation circuit 1R is formed so as to be a closed circuit by connecting coupling portions 1C and 1D of a catheter to each other by using a tube 1T which is separately prepared and is indicated by the dotted line. The inside of the closed circulation circuit 1R is filled with a physiological salt solution.

Subsequently, after the circulation circuit 1R is filled with a physiological salt solution, in Step SR2 in FIG. 4, the venous tube 11 and the vein side catheter 5 are connected to each other by using the coupling portion 1C, and the arterial tube 12 and the artery side catheter 6 are connected to each other by using the coupling portion 1D. In Step SR3 in FIG. 4, a manipulator (engineer) clamps the intermediate portion of the arterial tube 12 by using forceps or the like, thereby closing the arterial tube 12 on the artery side.

In Step SR4 in FIG. 4, a manipulator (engineer) raises the rotation speed of the drive motor 4 to 1,000 rpm via the control unit 100. Then, in Step SR5 in FIG. 4, a manipulator releases the clamped intermediate portion of the arterial tube 12 so as to open the arterial tube 12. A manipulator additionally raises the rotation speed of the drive motor 4, thereby starting circulation inside the circulation circuit 1R.

In this manner, the preparation before starting the extracorporeal circulation manipulation is performed by circulating a physiological salt solution inside the circulation circuit 1R. However, a rotation speed of the drive motor 4 suitable for a procedure varies depending on the condition of a patient, the policy of a hospital, or the like.

Figure 5:
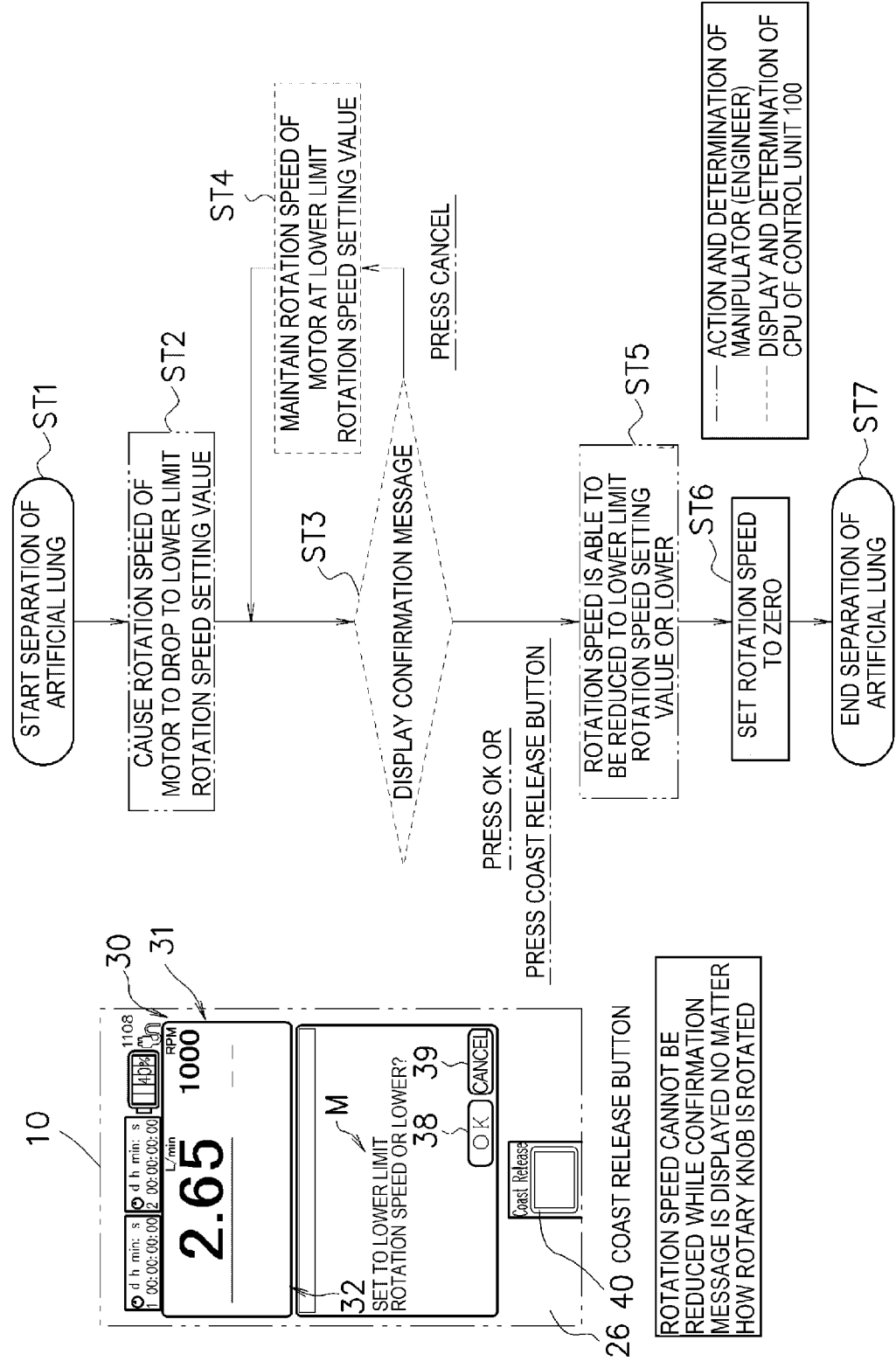
FIG. 5 is a flow chart illustrating an example of an operation while an artificial lung is separated.

Subsequently, with reference to FIGS. 3(B) and 5, description will be given regarding an operational example in which the artificial lung 2 is separated from the extracorporeal circulator 1 illustrated FIG. 1. FIG. 5 is a flow chart illustrating an example of an operation while the artificial lung 2 is separated from the circulation circuit 1R illustrated FIG. 1.

In Step ST1 in FIG. 5, work of separating the used artificial lung 2 from the circulation circuit 1R illustrated in FIG. 1 starts. In Step ST2, while the drive motor 4 illustrated in FIG. 1 rotates, that is, while the centrifugal pump 3 rotates, a manipulator (engineer) rotates the rotary knob 72 of the rotary manipulation section 51 illustrated in FIG. 1 in the counterclockwise direction CCW so as to cause the rotation speed of the drive motor 4 to drop to the above-described lower limit rotation speed setting value (for example, 1,000 rpm).

In this manner, when the rotation speed of the drive motor 4 drops to the above-described lower limit rotation speed setting value, in Step ST3, as illustrated in FIG. 5, in accordance with a command of the control unit 100 in FIG. 1, the display section 30 displays "Set to Lower Limit Rotation Speed or Lower?" which is the confirmation message M.

In the above-described Step ST3 in FIG. 5, in a state where the confirmation message M is displayed, no matter how a manipulator rotates the rotary knob 72 illustrated in FIG. 1 in the counterclockwise direction CW, the rotation speed of the drive motor 4 cannot be reduced below the lower limit setting value. In Step ST3, in a state where the confirmation message M is displayed, when a manipulator presses the "CANCEL" button 39 in the display section 30, the process proceeds to Step ST4.

In Step ST4, since a manipulator cancels the confirmation message M of "Set to Lower Limit Rotation Speed or Lower?" by pressing the "CANCEL" button 39, the rotation speed is in a state of not being allowed to be reduced to the lower limit rotation speed or lower. Therefore, the control unit 100 maintains the rotation speed of the drive motor 4 at the lower limit rotation speed setting value (for example, 1,000 rpm) with no change.

On the contrary, in Step ST3 illustrated in FIG. 5, in a state where the confirmation message M of "Set to Lower Limit Rotation Speed or Lower?" is displayed, when a manipulator presses the "OK" button 38 of the display section 30 or presses the coast release button 40, the process proceeds to Step ST5.

In Step ST5, a manipulator presses the "OK" button 38 of the display section 30 or presses the coast release button 40, and the manipulator agrees to the confirmation message M of "Set to Lower Limit Rotation Speed or Lower?". Thus, the rotation speed is in a state of being able to be reduced to the lower limit rotation speed or lower. Accordingly, since a manipulator can instruct the control unit 100 by rotating the rotary knob 72 in the counterclockwise direction CCW, the control unit 100 can reduce the rotation speed of the drive motor 4 to the above-described lower limit rotation speed setting value (for example, 1,000 rpm) or lower.

Thereafter, since the control unit 100 can reduce the rotation speed of the drive motor 4 to the above-described lower limit rotation speed setting value (for example, 1,000 rpm) or lower, and the engineer can set the rotation speed to zero in Step ST6, while being in such a state, a manipulator can separate the artificial lung 2 from the circulation circuit 1R in Step ST7.

As described above, when separating the artificial lung 2 from the extracorporeal circulator 1 illustrated in FIG. 1, a manipulator checks the displayed confirmation message M which is displayed by the display section 30 illustrated in FIG. 5 and the manipulator agrees thereto. Therefore, after a manipulator presses the "OK" button 38 of the display section 30 or presses the coast release button 40 thereof illustrated in FIG. 5, in a state where the rotation speed of the drive motor 4 is reduced, the manipulator can separate the artificial lung 2 from the circulation circuit 1R.

In this manner, unless a manipulator presses the "OK" button 38 or the coast release button 40 after having checked the displayed confirmation message M illustrated in FIG. 5 and having agreed thereto, the artificial lung 2 cannot be detached. Accordingly, it is possible to eliminate the occurrence of erroneous detachment manipulation when separating the artificial lung 2, that is, erroneous detachment of the artificial lung 2 intended by a manipulator before the rotation speed of the drive motor 4 is set to the above-described lower limit rotation speed setting value (for example, 1,000 rpm) or lower.

Figure 6:
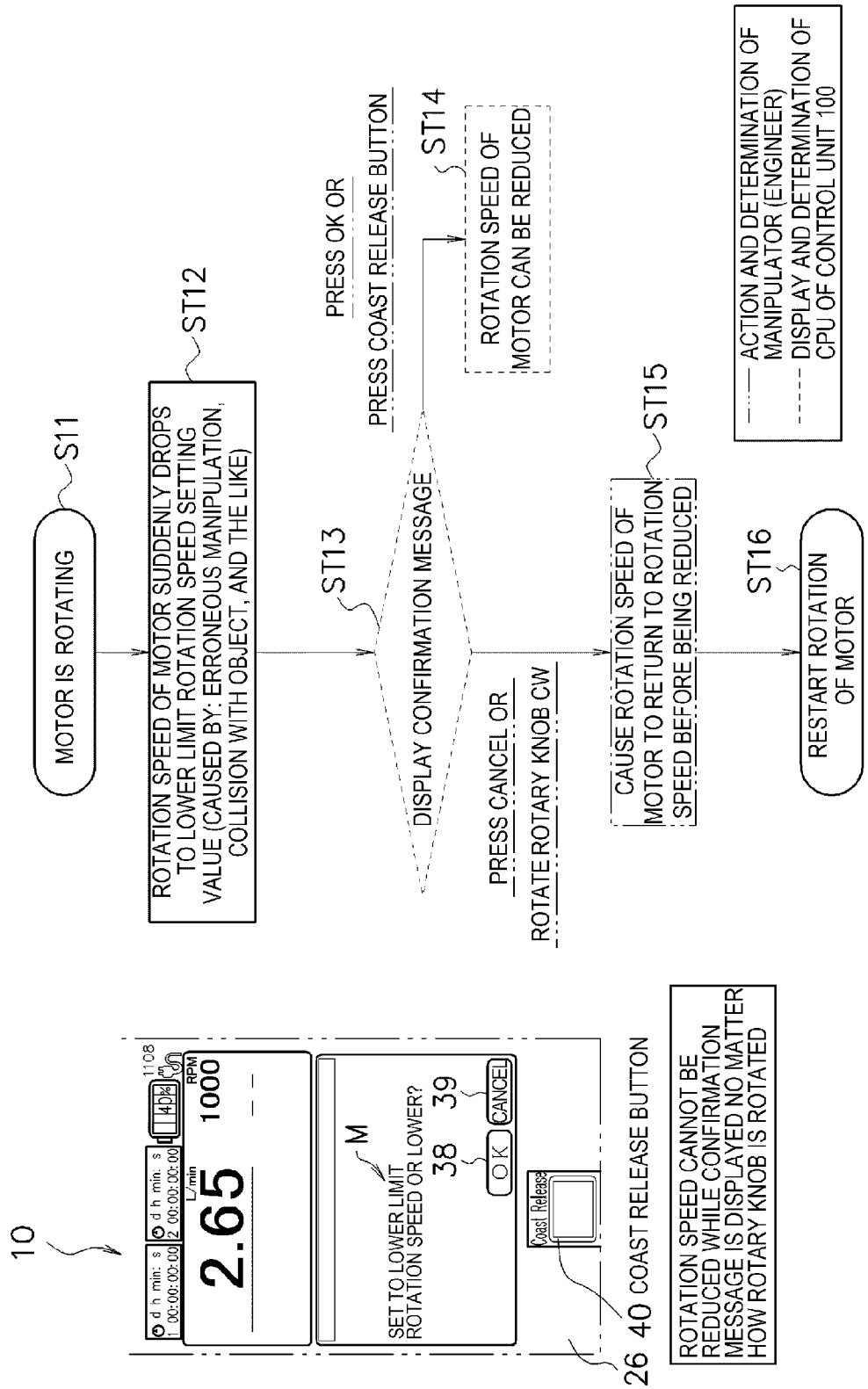
FIG. 6 is a flow chart illustrating an example of an operation to be performed when erroneous manipulation occurs in the extracorporeal circulator.

Subsequently, with reference to FIG. 6, description will be given regarding an example of an operation required to be performed when erroneous manipulation occurs in the extracorporeal circulator 1. FIG. 6 is a flow chart illustrating the example of the operation to be performed when erroneous manipulation occurs in the extracorporeal circulator 1. While the drive motor 4 (the centrifugal pump 3) rotates in Step ST11 in FIG. 6, in a case where the rotation speed of the drive motor 4 suddenly and erroneously drops to the above-described lower limit rotation speed setting value or lower for some reason in Step ST12, the process proceeds to Step ST13.

For example, the aforementioned some reason includes a case where a manipulator forgets the numerical value of the lower limit rotation speed setting value to be maintained and sets an erroneous numerical value of the lower limit rotation speed setting value, a case where the body of a manipulator erroneously comes into contact with the rotary knob 72 for setting the rotation speed illustrated in FIG. 1 and the rotary knob 72 rotates so that the rotation speed of the drive motor 4 is set to the lower limit rotation speed setting value or lower, a case where an object falls and hits the rotary knob 72 and the rotary knob 72 rotates so that the rotation speed of the drive motor 4 is set to the lower limit rotation speed setting value or lower, and the like.

In Step ST12 in FIG. 6, as described above, when the rotation speed of the drive motor 4 suddenly drops to the above-described lower limit rotation speed setting value for some reason, in Step ST13 in FIG. 6, the control unit 100 in FIG. 1 causes the display section 30 to display "Set to Lower Limit Rotation Speed or Lower?" which is the confirmation message M. In other words, even though control unit 100 receives a command via the rotary knob to adjust the rotation speed to a value below the lower limit rotation speed, control unit 100 maintains the rotation speed at the lower limit. Thus, control unit 100 may store a setting value for the lower limit rotation speed having a default value or configured by a manipulator (engineer) in preparation for the cardiac surgery.

As illustrated in FIG. 6, in a state where the confirmation message M of "Set to Lower Limit Rotation Speed or Lower?" is displayed, no matter how a manipulator rotates the rotary knob 72 illustrated in FIG. 1 in the counterclockwise direction CCW, the rotation speed of the drive motor 4 cannot be reduced.

In Step ST13, in a state where the confirmation message M of "Set to Lower Limit Rotation Speed or Lower?" is displayed, when a manipulator presses the "OK" button 38 or presses the coast release button 40, the process proceeds to Step ST14. In Step ST14, a manipulator agrees to the confirmation message M of "Set to Lower Limit Rotation Speed or Lower?", and the rotation speed is in a state of being able to be reduced to the lower limit rotation speed or lower. Accordingly, in Step ST14, since a manipulator can instruct the control unit 100 by rotating the rotary knob 72 in the counterclockwise direction CCW, the rotation speed of the drive motor 4 can be reduced to the above-described lower limit rotation speed setting value (for example, 1,000 rpm) or lower.

On the contrary, in Step ST13 illustrated in FIG. 6, in a state where the confirmation message M of "Set to Lower Limit Rotation Speed or Lower?" is displayed, when a manipulator presses the "CANCEL" button 39 of the display section 30, the process proceeds to Step ST15.

In Step ST15, a manipulator can raise the rotation speed by cancelling the confirmation message M of "Set to Lower Limit Rotation Speed or Lower?" or rotating the rotary knob 72 in the clockwise direction CW, and thus, the rotation speed is in a state of not being allowed to being reduced to the lower limit rotation speed or lower. Therefore, a manipulator can instruct the control unit 100 by rotating the rotary knob 72 so that the control unit 100 can cause the rotation speed of the drive motor 4 to return from a state where the rotation speed has suddenly dropped to the lower limit rotation speed setting value in Step ST12 to the rotation speed before being reduced to the lower limit rotation speed setting value (before the rotation speed suddenly drops), for example, 2,200 rpm. In Step ST16, as described above, a manipulator can restore the drive motor 4 so as to rotate at the rotation speed of the drive motor 4 before the rotation speed is reduced, for example, 2,200 rpm.

In this manner, after a manipulator checks the displayed confirmation message M illustrated in FIG. 5, when the manipulator presses the "OK" button 38 or presses the coast release button 40, the rotation speed of the drive motor 4 can be reduced. Therefore, rotation of the drive motor 4 can be stopped in response to a case of erroneous manipulation of the rotary knob 72. In addition, when a manipulator presses the "CANCEL" button 39, in Step ST15, in response to a case of erroneous manipulation of the rotary knob 72, it is possible to cause the rotation speed of the drive motor 4 to return to the rotation speed before having suddenly dropped and to restore the operation of the circulation circuit 1R.

Figure 7:
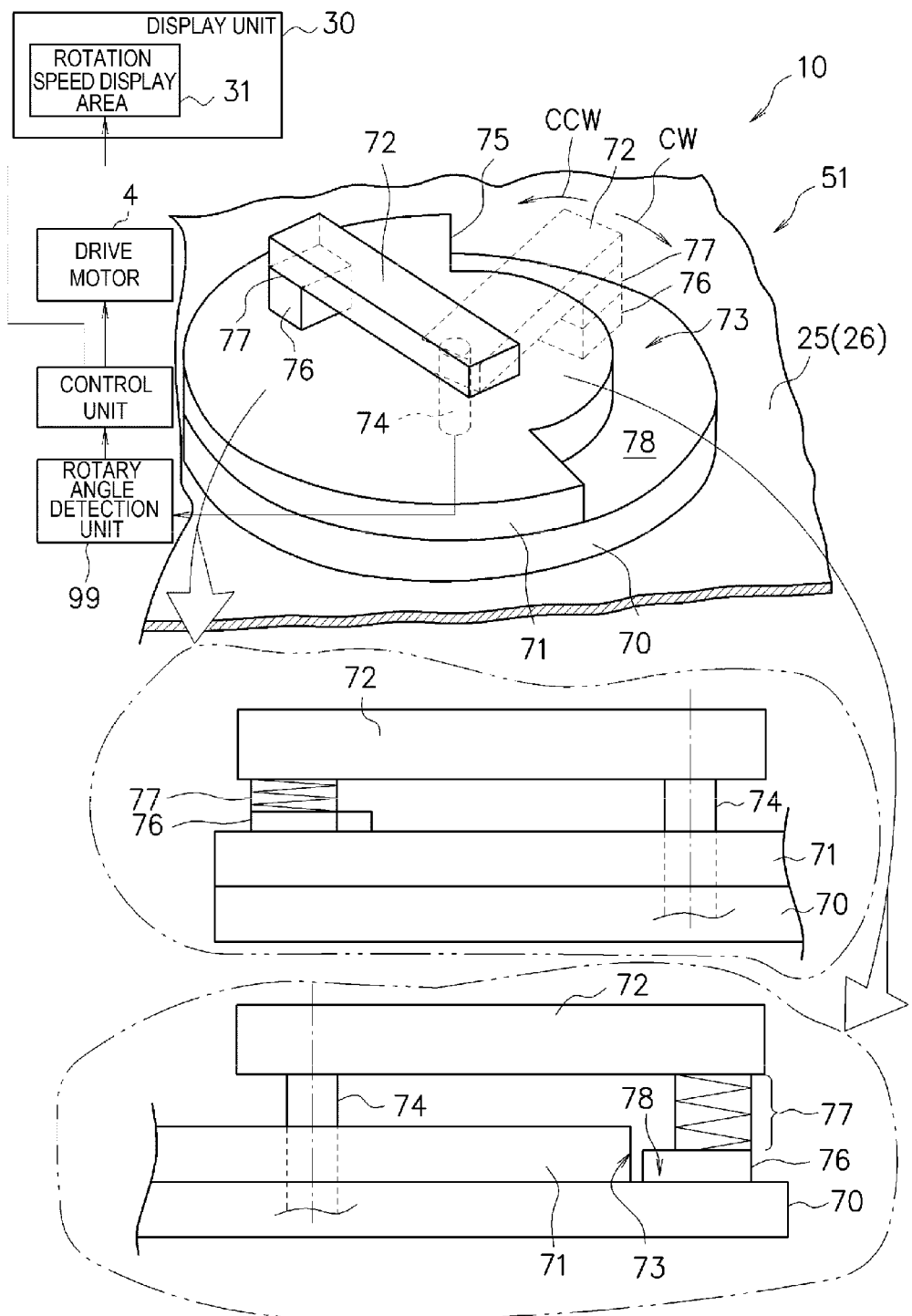
FIG. 7 is a perspective view illustrating a structure example of a rotary manipulation section.
Figure 8:
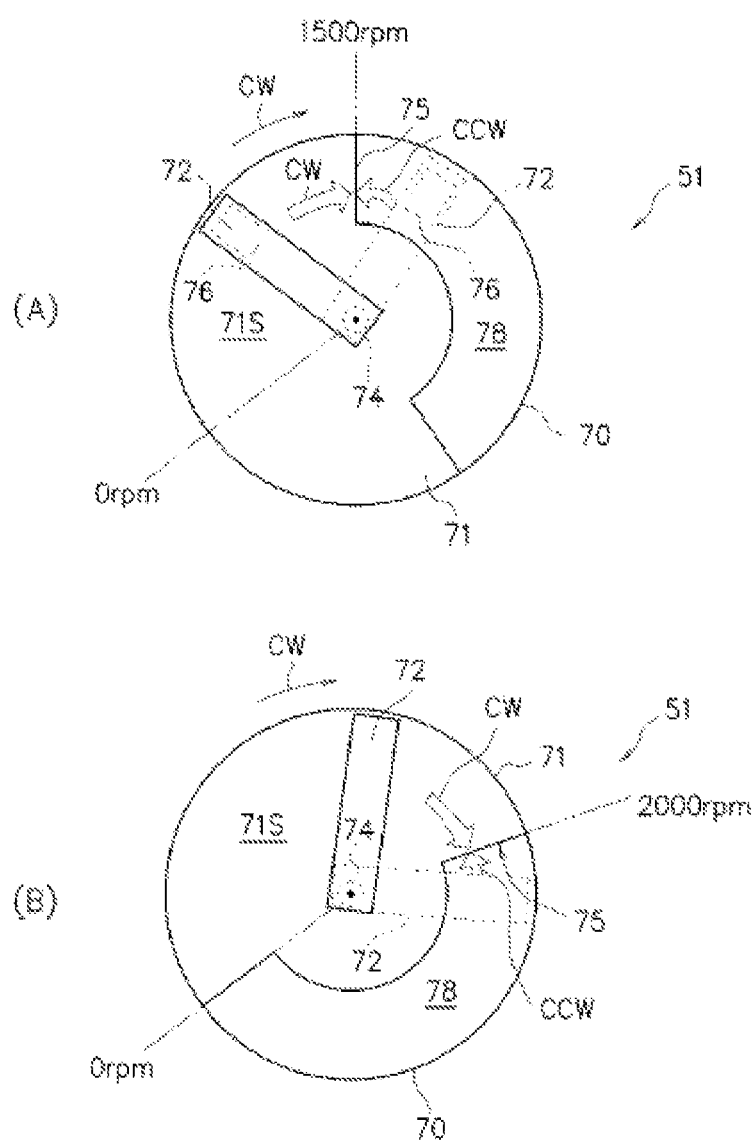
FIG. 8 is a diagram illustrating a manipulation example of a rotary knob of the rotary manipulation section illustrated in FIG. 7.

Subsequently, with reference to FIGS. 7 and 8, description will be given regarding a mechanical structure example of the rotary manipulation section 51 illustrated in FIG. 1. In this embodiment of rotary manipulation section 51, a lower limit rotation speed setting value does not have to be stored or enforced by control unit 100 because the lower limit setting value is instead enforced by rotary manipulation section 51. FIG. 7 is a perspective view illustrating the structure example of the rotary manipulation section 51, and FIG. 8 is a diagram illustrating a manipulation example of the rotary knob 72 of the rotary manipulation section 51 illustrated in FIG. 7.

The rotary manipulation section 51 illustrated in FIG. 7 is provided in the front surface portion 26 of the case 25 of the controller 10. The rotary manipulation section 51 has a disk-shaped fixed portion 70, a rotary portion 71 which is rotatably arranged on the fixed portion 70, and the rotary knob 72.

The fixed portion 70 illustrated in FIG. 7 is fixed to the front surface portion 26 of the case 25. As a manipulator holds the rotary portion 71 with fingers, the rotary portion 71 rotates centering around an axis portion 74 along the clockwise direction CW and the counterclockwise direction CCW with respect to the fixed portion 70 so that the rotary portion 71 can be positioned. The rotary portion 71 is a disk-shaped member. However, the rotary portion 71 has a fan-shaped cut-off portion 73. Since the rotary portion 71 has the cut-off portion 73, one end portion of the cut-off portion 73 becomes an erroneous operation prevention portion which is described later. The erroneous operation prevention portion 75 is provided in the rotary portion 71 in order to stop the rotary knob 72 from rotating in the counterclockwise direction CCW further than the position of the erroneous operation prevention portion 75.

As illustrated in FIG. 7, the one end portion side of the rotary knob 72 is attached to the upper end portion of the axis portion 74. As a manipulator holds the rotary knob 72 with fingers, the rotary knob 72 rotates along the clockwise direction CW and the counterclockwise direction CCW with respect to the fixed portion 70 and the rotary portion 71 so that the rotary knob 72 can be positioned. The inner surface on the other end portion side of the rotary knob 72 includes a stopper member 76 and a spring 77 which is a biasing member. The stopper member 76 is attached to the inner surface on the other end portion side of the rotary knob 72 via the spring 77.

The top surface of the fixed portion 70 which is a portion exposed through the cut-off portion 73 of the rotary portion 71 functions as a flat guide surface 78 for guiding the stopper member 76 of the rotary knob 72 along the clockwise direction CW and the counterclockwise direction CCW.

As illustrated in FIG. 7, when the rotary knob 72 rotates in the clockwise direction CW or the counterclockwise direction CCW, a rotary angle of the rotary knob 72 is detected by a rotary angle detection unit 99. As the rotary angle detection unit 99, for example, it is possible to employ a rotary encoder.

The control unit 100 is notified of the rotary angle of the rotary knob 72 detected by the rotary angle detection unit 99 illustrated in FIG. 7. The control unit 100 includes a corresponding table indicating relationships of the rotation speeds of the drive motor 4 which respectively correspond to the rotary angles of the rotary knob 72. Therefore, the control unit 100 can cause the rotation speed display area 31 of the display section 30 illustrated in FIG. 3 to display 1,000 rpm, for example, which is the rotation speed of the drive motor 4 on the basis of the rotary angle of the rotary knob 72.

FIG. 8(A) illustrates a state where the rotary portion 71 rotates in the clockwise direction CW with respect to the fixed portion 70 so that the erroneous operation prevention portion 75 of the rotary portion 71 is manually adjusted by a manipulator to a position of 1,500 rpm. FIG. 8(B) illustrates a state where the rotary portion 71 has been manually rotated by the manipulator by an additional amount in the clockwise direction CW with respect to the fixed portion 70 so that the erroneous operation prevention portion 75 of the rotary portion 71 is positioned at a position of 2,000 rpm.

In the state illustrated in FIG. 8(A), when the rotary knob 72 rotates in the clockwise direction CW from the position indicated by the solid line to the position indicated by the dotted line, the position of the stopper member 76 of the rotary knob 72 changes from the state illustrated in FIG. 7(A) to the state illustrated in FIG. 7(B). In other words, in the state illustrated in FIG. 7(A), since the stopper member 76 is interposed between the inner surface of the rotary knob 72 and a guide surface 71S on the front surface of the rotary portion 71 against the force of the spring 77, the stopper member 76 is in a state of compressing the spring 77. Then, in the state illustrated in FIG. 7(B), since the stopper member 76 is guided by the guide surface 78 of the fixed portion 70, the spring 77 presses the stopper member 76 onto the guide surface 78.

Incidentally, in the state illustrated in FIG. 8(A), when a manipulator intends to cause the rotary knob 72 to return from the dotted line position in the counterclockwise direction CCW, the stopper member 76 directly abuts on the erroneous operation prevention portion 75 of the rotary portion 71. Accordingly, the rotary knob 72 cannot return any farther from the position thereof by rotating in the counterclockwise direction CCW. In this example, since the erroneous operation prevention portion 75 of the rotary portion 71 is set to the position of 1,500 rpm, for example, a manipulator cannot cause the rotation speed of the drive motor 4 (the centrifugal pump 3) illustrated in FIG. 1 to be 1,500 rpm or lower.

In addition, in the state illustrated in FIG. 8(B), when the rotary knob 72 rotates in the clockwise direction CW from the position indicated by the solid line so as to be at the position indicated by the dotted line, the position of the stopper member 76 of the rotary knob 72 similarly changes from the state illustrated in FIG. 7(A) to the state illustrated in FIG. 7(B).

Incidentally, in the state illustrated in FIG. 8(B), when a manipulator intends to cause the rotary knob 72 to return from the dotted line position in the counterclockwise direction CCW, the stopper member 76 directly abuts on the erroneous operation prevention portion 75 of the rotary portion 71. Accordingly, the rotary knob 72 cannot return any further in the counterclockwise direction CCW from the position thereof. In this example, since the erroneous operation prevention portion 75 of the rotary portion 71 is set to the position of 2,000 rpm, for example, a manipulator cannot cause the rotation speed of the drive motor 4 (the centrifugal pump 3) illustrated in FIG. 1 to be 2,000 rpm or lower.

As described above in the structure example of the rotary manipulation section 51, in a case where the lower limit rotation speed setting value is set to 1,500 rpm or 2,000 rpm, for example, the structure stops the rotary knob 72 from rotating in the counterclockwise direction CCW so that a manipulator cannot cause the rotary knob 72 to return in the counterclockwise direction CCW so as to be 1,500 rpm or lower, or 2,000 rpm or lower.

In addition, the lower limit rotation speed setting value is changeable by manipulating the rotary portion 71 so as to rotate with respect to the fixed portion 70. In addition, when the stopper member 76 is pushed upward to the inner surface side of the rotary knob 72 against the force of the spring 77, the stopper member 76 can move from the guide surface 78 of the fixed portion 70 to the guide surface 71S on the front surface of the rotary portion 71. Accordingly, even though the erroneous operation prevention portion 75 of the rotary portion 71 illustrated in FIGS. 8(A) and 8(B) is present, the rotary knob 72 can rotate in the counterclockwise direction CCW, e.g., when a coast release is performed in order to separate the patient from circulation circuit 1R.

The extracorporeal circulator 1 according to the embodiment of the present invention is an extracorporeal circulator in which the pump 3 arranged in the circulation circuit 1R is driven by the motor 4 so as to circulate blood of a patient through the artificial lung 2.

The extracorporeal circulator 1 includes the control unit 100, the manipulation section of the control unit 100 (for example, the rotary manipulation section 51) which is able to set the lower limit rotation speed setting value of the motor in a changeable manner, and the rotation speed display section 60 which is able to display the lower limit rotation setting value of the motor 4 in accordance with a command of the control unit 100. The lower limit rotation speed setting value is the minimum rotation speed for preventing backflow of blood inside the circulation circuit 1R when a manipulator performs manipulation so as to operate the motor 4 and to cause the blood to return from the artificial lung 2 to the inside of the body of the patient P that is a patient while a command is applied to the control unit 100 so that the rotation speed of the motor 4 can be changed.

In this manner, the lower limit rotation speed setting value of the motor 4 can be changed by using the manipulation section 51, and the rotation speed display section 60 can display the lower limit rotation speed setting value of the motor 4. Therefore, it is possible to prevent backflow of blood from occurring in the circulation circuit and affecting the body of a patient and to safely perform extracorporeal circulation manipulation during a surgical operation while erroneous manipulation causing the rotation speed of the motor 4 to drop to the lower limit rotation speed or lower in the extracorporeal circulator 1 is prevented.

In the display section 30, in a case where the rotation speed of the motor 4 is raised from zero rpm and exceeds the lower limit rotation speed setting value, before the rotation speed of the motor 4 is reduced to the lower limit rotation speed setting value or lower, the control unit 100 causes the display section 30 to display the confirmation message M. In this manner, since the control unit 100 causes the display section 30 to display the confirmation message M before the rotation speed of the motor 4 is reduced to the lower limit rotation speed setting value or lower, the confirmation message M allows a manipulator to visually check whether the rotation speed of the motor 4 is intended to beset to the lower limit rotation speed setting value or lower, and thus, it is possible to prevent the rotation speed of the motor 4 from being erroneously manipulated and being set to the lower limit rotation speed setting value or lower.

When the confirmation message displayed by the display section 30 is received, the control unit allows the rotation speed of the motor to be reduced to the lower limit rotation speed setting value or lower. In this manner, in a case where the confirmation message displayed by the display section 30 is received, a manipulator can reduce the rotation speed of the motor to the lower limit rotation speed setting value or lower, and thus, it is possible to prevent the rotation speed of the motor from being erroneously manipulated and being set to the lower limit rotation speed setting value or lower.

The manipulation section is a rotary manipulation section having the rotary knob which can be rotatably manipulated as a manipulator pinches the rotary knob with fingers. The rotation speed display section 60 which is lit to display the rotation speed of the motor is provided on the periphery of the rotary knob. In this manner, since the rotation speed display section 60 is provided on the periphery of the rotary knob 72, when a manipulator manipulates the rotary knob 72, it is possible to visually check the rotation speed of the motor due to lighting of the rotation speed display section 60.

The rotary manipulation section has the fixed portion; the rotary portion which is provided so as to be rotatable with respect to the fixed portion in order to arbitrarily set the lower limit rotation speed setting value of the motor; and the rotary knob which is provided so as to be rotatable with respect to the rotary portion and the fixed portion, and is rotatably manipulated by being pinched by a manipulator in order to set the rotation speed of the motor and apply a command to the control unit. The rotary portion has the erroneous manipulation prevention portion which abuts on the rotary knob so as to prevent the rotary knob from erroneously rotating and being set to the lower limit rotation speed setting value or lower of the motor. In this manner, since the rotary portion has the erroneous manipulation prevention portion which abuts on the rotary knob so as to prevent the rotary knob from erroneously rotating to the lower limit rotation speed setting value or lower of the motor, it is possible to mechanically and reliably prevent the rotation speed of the motor from being erroneously manipulated and being set to the lower limit rotation speed setting value or lower.

The present invention is not limited to the above-described embodiment and various changes can be made without departing from the scope of Claims.

A rotation drive unit may be a "motor", a "rotary pump", or a rotation driver in a case where "a motor and a pump" are combined together, as described above.

Each configuration of the above-described embodiment can be partially omitted, or can be arbitrarily combined together so as to be different from the above-described embodiment.

The rotation speed display section 60 may have a different shape such as a linear shape, and an elliptical shape, which are arbitrarily formed, in addition to being annularly formed as described in the illustrated example.

What is claimed is:

1. An extracorporeal circulator driven by a rotation drive unit to circulate blood of a patient outside a body, the extracorporeal circulator comprising:
a control unit coupled to the rotation drive unit to control an actual rotation speed of the rotation drive unit;
a manipulation section coupled to the control unit to manually adjust a speed setting request provided to the control unit, wherein the control unit controls the rotation speed of the rotation drive unit subject to a lower limit rotation speed setting value; and
a rotation speed display section that displays the lower limit rotation setting value of the rotation drive unit in accordance with a command of the control unit,
wherein the lower limit rotation speed setting value is a minimum rotation speed for preventing backflow of the blood inside the circulator so as to operate the rotation drive unit and to cause the blood to return to an inside of the body of the patient, and
wherein after a rotation speed of the rotation drive unit is raised above the lower limit rotation speed setting value, the control unit causes the display section to display a confirmation message in response to a manually adjusted speed setting request at or below the lower limit rotation speed setting value.

2. The extracorporeal circulator according to claim 1, wherein when the confirmation message displayed by the display section is received, the control unit allows the rotation speed of the rotation drive unit to be reduced to the lower limit rotation speed setting value or lower in response to a manual acknowledgement.

3. An extracorporeal circulator driven by a rotation drive unit to circulate blood of a patient outside a body, the extracorporeal circulator comprising:
a control unit coupled to the rotation drive unit to control an actual rotation speed of the rotation drive unit; and
a manipulation section coupled to the control unit to manually adjust a speed setting request provided to the control unit,
wherein the rotary manipulation section has a fixed portion; a rotary portion which is provided so as to be rotatable with respect to the fixed portion in order to arbitrarily set the lower limit rotation speed setting value of the rotation drive unit; and the rotary knob which is provided so as to be rotatable with respect to the rotary portion and the fixed portion, and is rotatably manipulated by being pinched by the manipulator in order to set the rotation speed of the rotation drive unit and to apply a command to the control unit, and
wherein the rotary portion has an erroneous manipulation prevention portion which abuts on the rotary knob so as to prevent the rotary knob from erroneously rotating and being set to the lower limit rotation speed setting value or lower of the rotation drive unit.

4. An extracorporeal circulator driven by a rotation drive unit to circulate blood of a patient outside a body, the extracorporeal circulator comprising:
  a control unit coupled to the rotation drive unit to control an actual rotation speed of the rotation drive unit;
  a manipulation section coupled to the control unit to manually adjust a speed setting request provided to the control unit, wherein the control unit controls the rotation speed of the rotation drive unit subject to a lower limit rotation speed setting value; and
  a rotation speed display section that displays the lower limit rotation setting value of the rotation drive unit in accordance with a command of the control unit,
  wherein the lower limit rotation speed setting value is a minimum rotation speed for preventing backflow of the blood inside the circulator so as to operate the rotation drive unit and to cause the blood to return to an inside of the body of the patient, and
  wherein the manipulation section is a rotary manipulation section having a rotary knob which is able to be rotatably manipulated as a manipulator pinches the rotary knob with fingers, and the rotation speed display section which is lit to display the rotation speed of the rotation drive unit is provided on the periphery of the rotary knob.

5. The extracorporeal circulator according to claim 4, wherein the rotation speed display section is comprised of a plurality of light emitters along the periphery of the rotary knob, each light emitters corresponding to a respective rotation speed, wherein a light emitter corresponding to the lower limit rotation setting value is continuously illuminated, and wherein a consecutively lit string of light emitters indicates the manually adjusted speed setting request.

* * * * *